(12) United States Patent
Fathallah et al.

(10) Patent No.: US 7,556,616 B2
(45) Date of Patent: Jul. 7, 2009

(54) MEDICAL DEVICE SYSTEM

(75) Inventors: Marwan A. Fathallah, Mundelein, IL (US); John S. Ziegler, Arlington Heights, IL (US); Todd J. Bakken, Madison, WI (US); Daniel J. Lee, Madison, WI (US)

(73) Assignee: Hospira, Inc., Lake Forest, IL (US)

( * ) Notice: Subject to any disclaimer, the term of this patent is extended or adjusted under 35 U.S.C. 154(b) by 1089 days.

(21) Appl. No.: 10/823,220

(22) Filed: Apr. 13, 2004

(65) Prior Publication Data

US 2005/0135047 A1    Jun. 23, 2005

Related U.S. Application Data

(63) Continuation-in-part of application No. 10/696,830, filed on Oct. 30, 2003.

(51) Int. Cl.
*A61M 37/00*    (2006.01)

(52) U.S. Cl. .................................................... 604/131

(58) Field of Classification Search ............. 604/65–67, 604/131, 250; 128/DIG. 12, DIG. 13; 24/455, 24/462, 563; 248/226.11, 316.1
See application file for complete search history.

(56) References Cited

U.S. PATENT DOCUMENTS

| | | |
|---|---|---|
| 1,749,491 A | 3/1927 | Kokay |
| 4,696,671 A | 9/1987 | Epstein et al. |
| 4,756,706 A | 7/1988 | Kerns et al. |
| 4,832,299 A | 5/1989 | Gorton et al. |
| 4,844,397 A | 7/1989 | Skakoon et al. |
| 5,169,106 A | 12/1992 | Rasmussen |
| 5,219,428 A | 6/1993 | Stern |
| 5,317,506 A | 5/1994 | Coutre et al. |
| 5,322,253 A | 6/1994 | Stevens |
| 5,326,059 A | 7/1994 | Pryor et al. |
| 5,332,184 A | 7/1994 | Davis |
| 5,358,205 A | 10/1994 | Starkey et al. |
| 5,378,231 A | 1/1995 | Johnson et al. |
| 5,417,395 A | 5/1995 | Fowler et al. |
| 5,431,509 A | 7/1995 | Anderson et al. |
| 5,445,621 A | 8/1995 | Poli et al. |
| D367,528 S | 2/1996 | Martson et al. |
| 5,601,445 A | 2/1997 | Schipper et al. |
| 5,626,151 A | 5/1997 | Linden |

(Continued)

FOREIGN PATENT DOCUMENTS

EP    0477551 B1    8/1991

*Primary Examiner*—Manuel A Mendez
(74) *Attorney, Agent, or Firm*—Michael R. Crabb

(57) ABSTRACT

A first portable medical device is adapted for use in an interlocking system for interlocking the first medical device to a second medical device. The first device includes a housing having opposite sides, a selective element, a blocking element, and an optional clamp mechanism. At least one of the opposite sides includes a matable element to detachably attach a second medical device. The selective element restricts the attachment of the second device to only one side of the first device. The blocking element prevents a third medical device from attaching to the first and second devices once the first and second devices are attached. The clamp restricts the attachment of the second device to only one side of the first device when the clamp is attached to a support member. The clamp permits slide-ratcheting axial movement of a clamp shaft.

25 Claims, 9 Drawing Sheets

U.S. PATENT DOCUMENTS

| | | |
|---|---|---|
| 5,713,856 A | 2/1998 | Eggers et al. |
| 5,733,061 A | 3/1998 | Child |
| 5,782,611 A | 7/1998 | Neftel et al. |
| 5,782,805 A | 7/1998 | Meinzer et al. |
| 5,941,846 A | 8/1999 | Duffy et al. |
| RE36,871 E | 9/2000 | Epstein et al. |
| 2001/0044602 A1 | 11/2001 | Angersbach et al. |

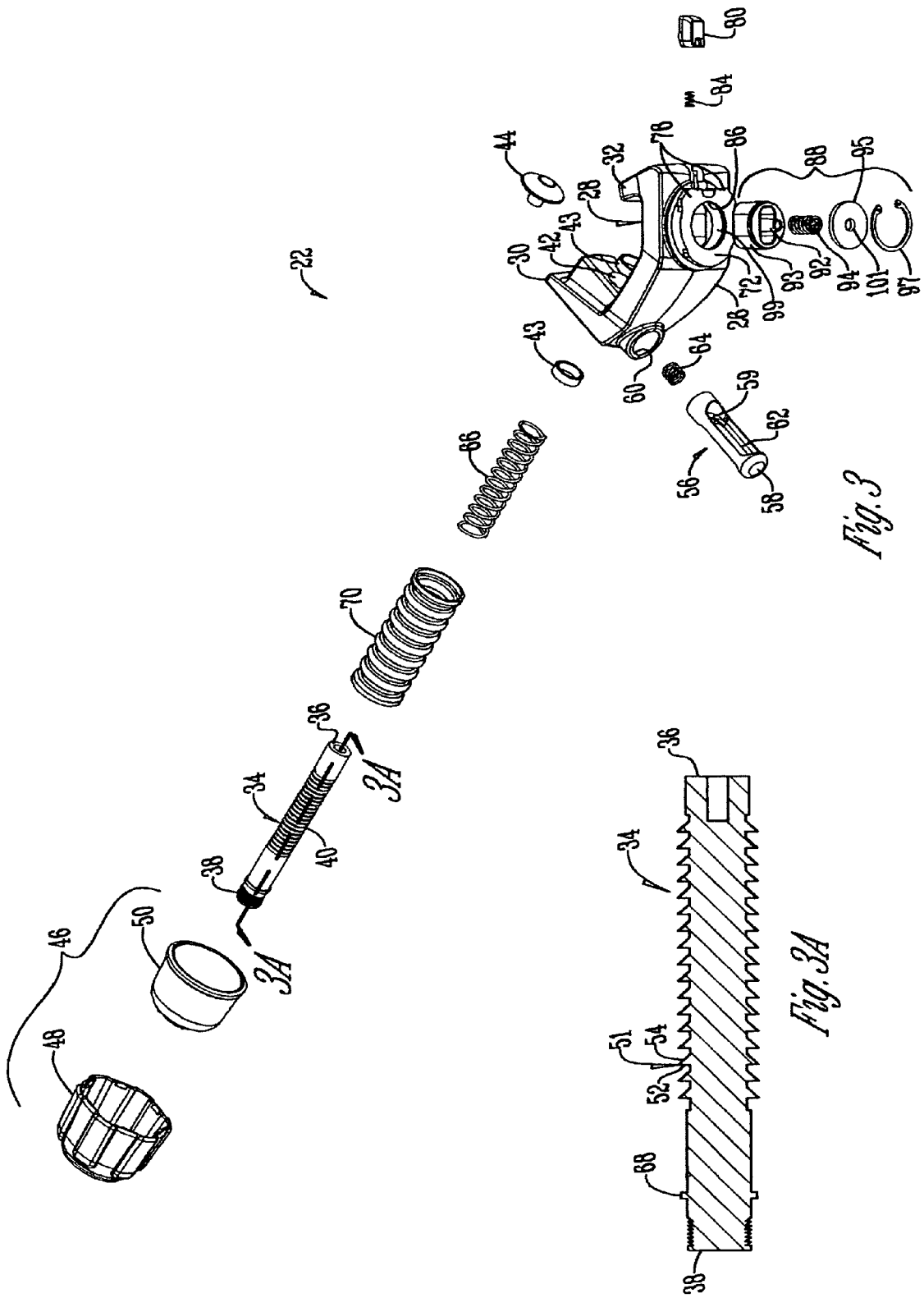

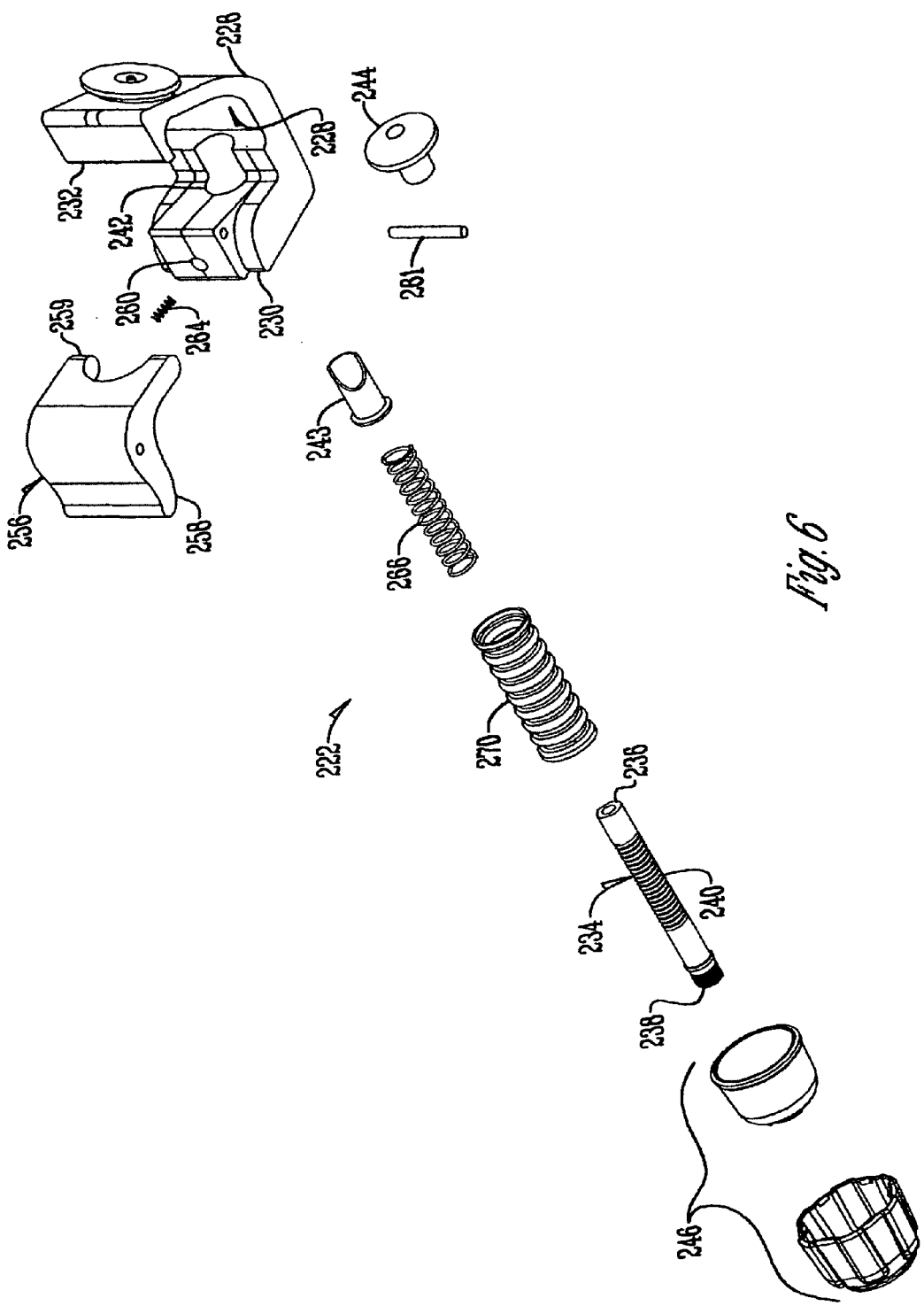

MEDICAL DEVICE SYSTEM

CROSS-REFERENCE TO RELATED APPLICATIONS

This application is a continuation-in-part of U.S. patent application Ser. No. 10/696,830, filed Oct. 30, 2003.

BACKGROUND OF THE INVENTION

The present invention generally relates to the field of medical devices, and more particularly to the field of point of care medical devices including but not limited to infusion pumps, monitors, and diagnostic equipment. The invention provides a portable point of care system that includes one or more medical devices mountable on a pole stand, bedrail or other supporting structure in close proximity to a patient. The invention includes means and methods for interlocking the medical devices together, preventing undesirable arrangements and combinations of medical devices, mounting the medical devices on the main supporting structure, and automatically providing wireless communication between the medical devices.

In modern medical practice a variety of diagnostic and therapeutic devices are used, sometimes to such a degree that floor and shelf space near the patient's bedside is at a premium. One known solution to the problem of mounting medical devices is the use a pole stand. Often such pole stands have wheels for the convenience of the patient or medical personnel in moving the devices where they are needed, but wheeled pole stands can become unbalanced upon, for example, crossing thresholds or exiting elevators.

Some manufacturers have mounted a central management unit and infusion pump modules in a vertically stacked configuration on a pole stand, as disclosed in U.S. Pat. Nos. 4,756,706 and 4,898,578. Vertically stacked configurations can make identification, routing and management of the associated intravenous (IV) tubes confusing and difficult. Manufacturers also have interlocked interchangeable independently functioning single channel pumps in a horizontal arrangement for attachment at a particular vertical location on a pole stand, as disclosed in U.S. Pat. No. 5,431,509. U.S. Pat. Nos. 5,713,856; 5,941,846 and 5,601,445 disclose a central control unit and a plurality of horizontally arranged detachable pump and/or sensor modules. Other manufacturers have developed multiple channel pumps, as disclosed in U.S. Pat. No. 5,378,231 and Des. 367,528. However, in the vast majority of applications a single channel pump or single pump module will suffice to meet the caregiver's needs, and customers generally are not inclined to pay the substantial premium needed to cover the manufacturing cost of a multiple channel pump or an elaborate interlocking means. Thus, there is a need for an improved system of medical devices.

A primary objective of the present invention is the provision of an improved system of interlockable portable medical devices that only allows two medical devices to be joined together.

Another objective of the present invention is the provision of an improved system of interlockable portable medical devices.

A further objective of the present invention is the provision of an improved clamp mechanism, for mounting a medical device to a support member, which restricts the attachment of a second medical device to only one side of a first medical device when the clamp mechanism is attached to a support member.

A still further objective of the present invention is the provision of an improved clamp mechanism that permits slide-ratcheting axial movement of the clamp shaft.

These and other objects will be apparent to those skilled in the art.

SUMMARY OF THE INVENTION

A first portable medical device is adapted for use in an interlocking system for interlocking the first medical device to a second medical device. The first device includes a housing having opposite sides, a selective element, a blocking element, a clamp mechanism, and wherein at least one of the opposite sides includes a first matable element to detachably interconnect a second medical device to the first medical device. The selective element restricts the attachment of the second device to only one of the opposite sides of the first device. The blocking element prevents a third medical device from attaching to either the first or second device once the first and second devices are attached. The clamp mechanism restricts the attachment of the second device to only one side of the first device when the clamp mechanism is attached to a support member. The clamp mechanism also permits slide-ratcheting axial movement of a clamp shaft.

BRIEF DESCRIPTION OF THE DRAWINGS

FIG. 3 is an exploded perspective view of a clamping mechanism of the present invention;

FIG. 3A is a cross sectional side view of the clamping mechanism of the present invention taken along line 3A-3A in FIG. 3;

FIG. 6 is an exploded perspective view of an alternative clamping mechanism of the present invention.

DETAILED DESCRIPTION OF THE PREFERRED EMBODIMENT(S)

Figure 1:
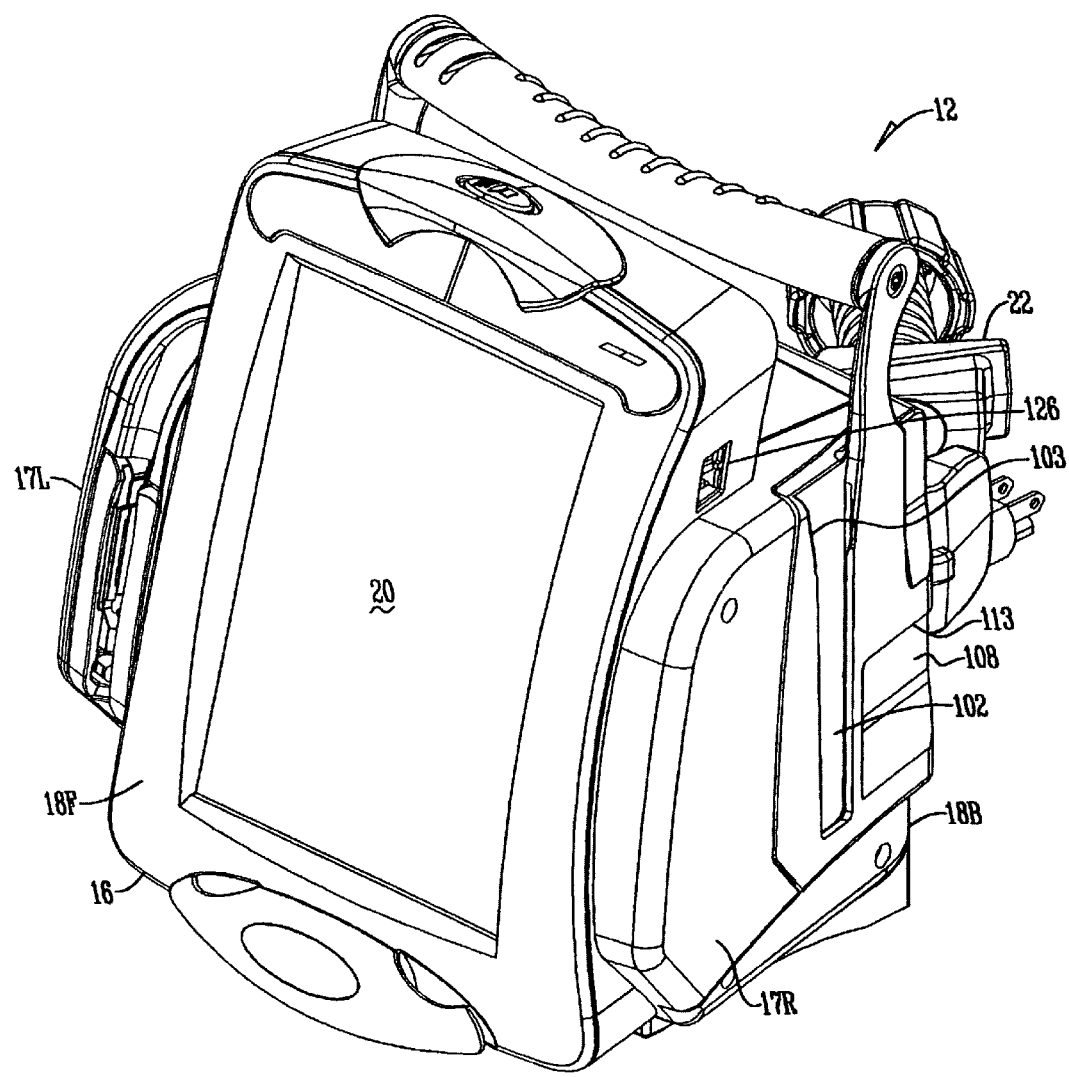
FIG. 1 is a front perspective view of a medical device adapted for use in a medical device system according to the present invention.

In the description and figures, components that are similar or substantially identical in function or structure are designated with similar or identical reference numerals.

The medical device system 10 (FIG. 2), 10A (FIG. 2A) of the present invention includes a plurality of portable medical devices 12 (FIG. 1) and 14 (FIG. 1A) or 14L and 14R (FIG. 2A) that are capable of being detachably interlocked together. Devices 12, 14, 14L, or 14R can be devices for performing similar tasks or devices for performing different tasks as described below. For the sake of brevity the devices 14L, 14R, which are labeled to indicate their respective positions on the left and right of the system 10A when viewed from the front, are sometimes referenced in a generic sense by reference numeral 14. In the context of the present invention, the term "medical device" includes without limitation a device that acts upon a cassette, reservoir, vial, syringe, or tubing to convey medication or fluid to or from a patient (for example, an infusion pump, a patient controlled analgesia (PCA) or pain management medication pump, or a suction pump), a monitor for monitoring patient vital signs or other parameters, or a diagnostic device.

For the purpose of exemplary illustration only, the medical devices 12, 14, 14L, and 14R are all disclosed as infusion pumps. More particularly, the medical device 12 can be a single channel infusion pump and the medical devices 14L and 14R can be dual channel infusion pumps. The pumps 12 and 14 have housings 16 and 16A respectively. Each housing 16, 16A includes generally opposite side walls 17L, 17R and generally opposite back and front walls 18B, 18F. A user interface touch screen 20 is mounted in the front wall of housing 16, 16A so as to be visible and accessible from the front of the device.

Figure 2:
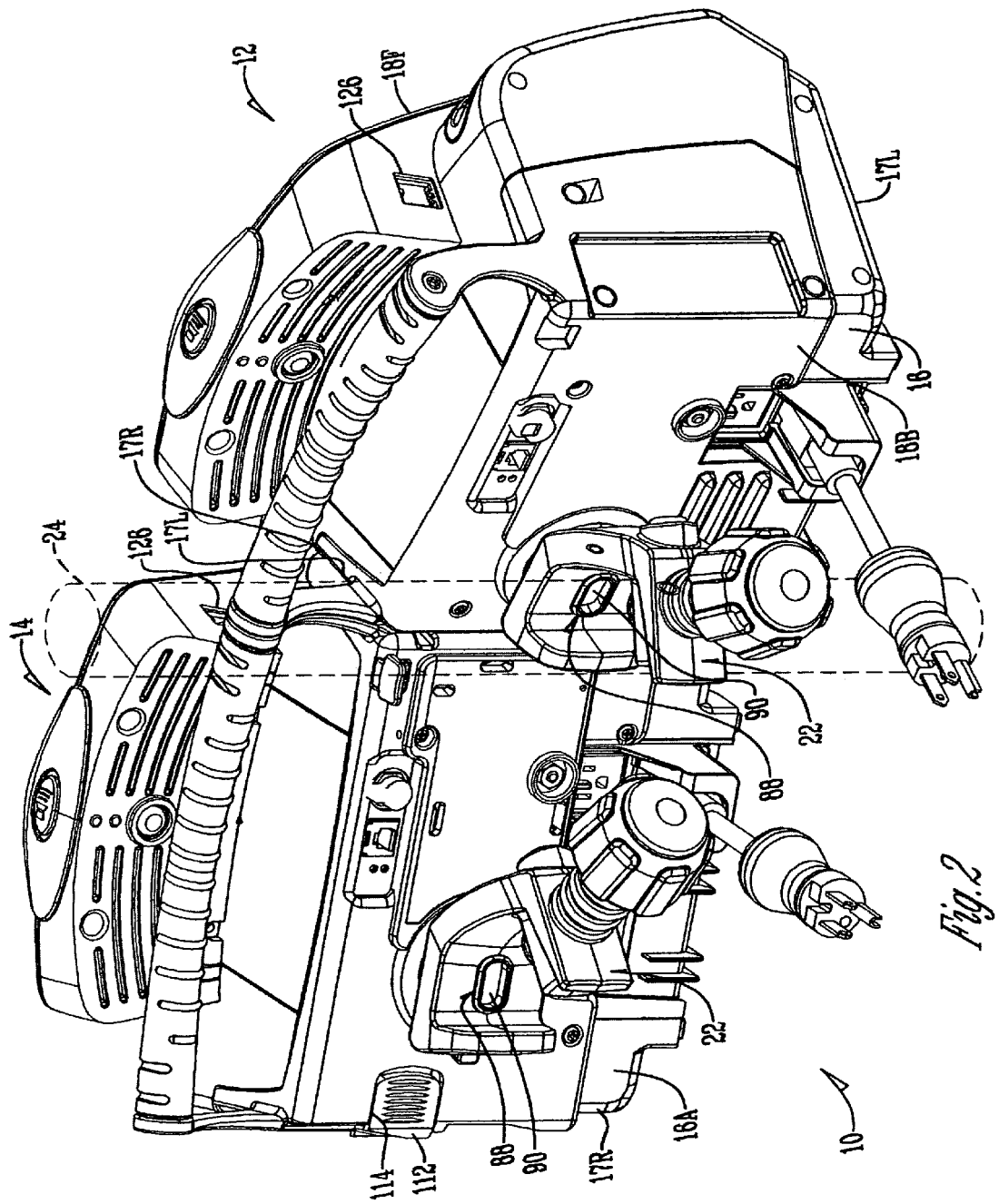
FIG. 2 is a rear perspective view of one embodiment of the medical device system of this invention wherein two medical devices are joined together in side-by-side relationship.
Figure 2A:
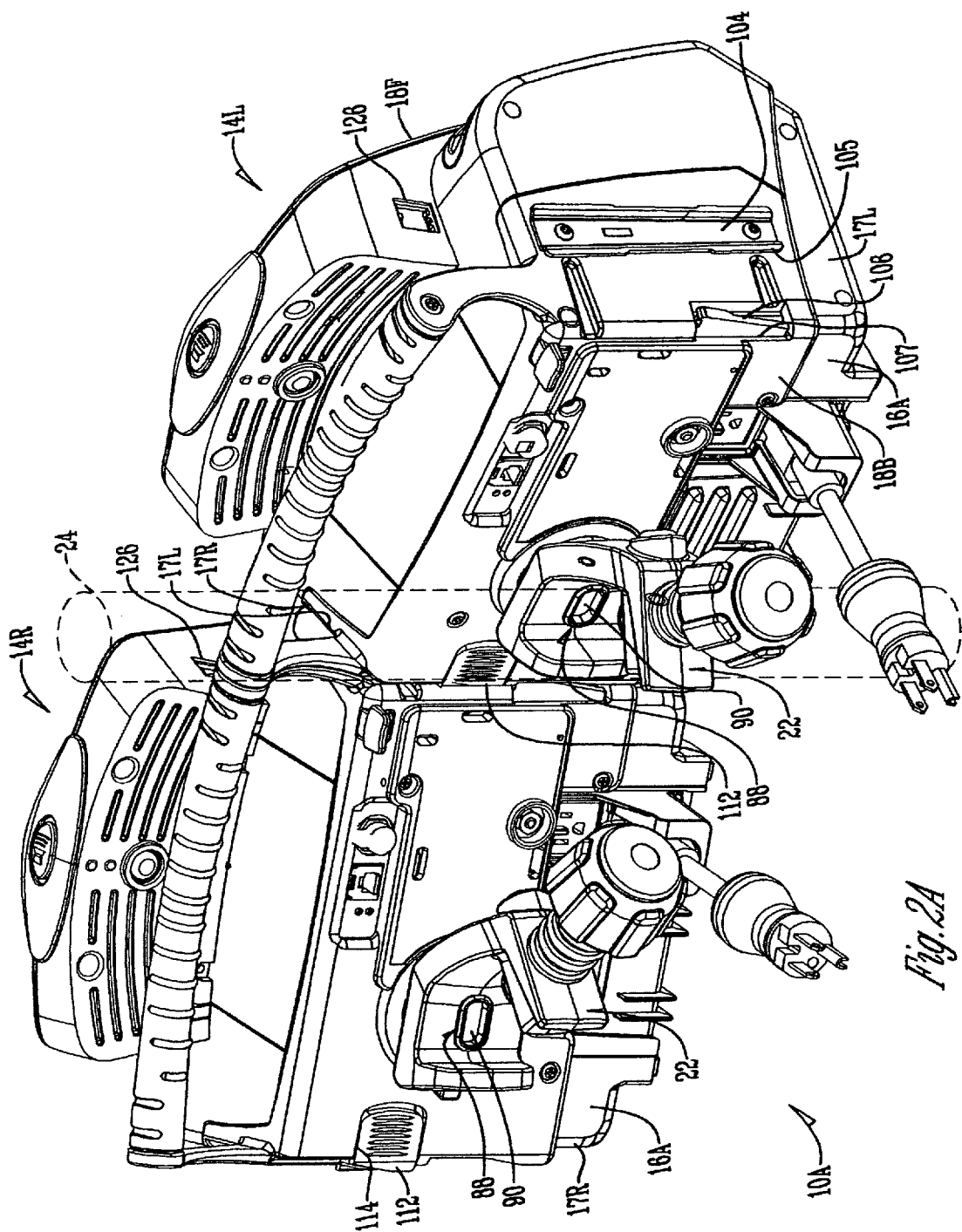
FIG. 2A is a rear perspective view of another embodiment of the medical device system of this invention wherein two medical devices are joined together in side-by-side relationship.

As best seen in FIGS. 2 and 2A, at least one, and more preferably both, of the medical devices or pumps 12, 14 has a releasable clamping mechanism 22 attached thereto for detachably mounting the device 12 or 14 to a support structure or member, such as a tabletop edge or pole 24. In the context of this invention, a "pole" should be understood to include without limitation an elongated bar, rail, tubular member, beam or pin on a pole stand, bed, wall or other structure for supporting the medical device. The pole 24 can be configured and oriented in a variety of known ways, including without limitation as a bed rail extending in a generally horizontal direction or as an upright tubular member extending in a generally vertical direction on a pole stand. For the sake of brevity only the clamping mechanism 22 on the pump 12 is described below, but the clamping mechanism 22 on pump 14, if provided, can be substantially identical.

As best seen in FIGS. 2, 2A, 3 and 3A, the clamping mechanism 22 of the present invention has a substantially rigid clamp body 26 that is pivotally and preferably removably attached to the pump housing 16 and includes a pole-receiving slot 28 for receiving the pole 24. The clamp body 26 defines generally opposing first and second jaws 30, 32 that at least partially surround the pole-receiving slot 28. One skilled in the art will appreciate that many different clamp body shapes can be utilized without detracting from the invention, including without limitation a generally L-shaped, U-shaped, J-shaped, G-shaped or. C-shaped clamp body.

A clamp shaft 34 is movably mounted on the first jaw 30. The clamp shaft 34 has opposite ends 36, 38 and a ratchet portion 40 therebetween. The first jaw 30 has a clamp shaft receiving hole 42 formed therein, and more preferably therethrough, for receiving bushings 43 and the ratchet portion 40 of the clamp shaft 34. The distal end 36 of the clamp shaft 34 extends from the first jaw 30 toward the second jaw 32. A pressure pad 44 connects, or more preferably attaches, to the distal end 36.

The proximal end 38 of the clamp shaft 34 has displacement means 46 connected thereto for selectively moving the clamp shaft 34 axially and applying a torque to the clamp shaft 34. While one skilled in the art will appreciate that the displacement means 46 for moving or turning the clamp shaft could include a hydraulic or pneumatic cylinder, electric stepper motor, or other powered displacement devices, a simple manual hand knob 48 can be connected to the clamp shaft 34, preferably to the proximal end 38 on the opposite side of the first jaw 30.

A clutch mechanism 50 can be operatively interposed between the knob 48 and the clamp shaft 34. The clutch mechanism 50 can be a ratchet type or any other known type for preventing the tightening torque applied to the clamp shaft from exceeding a predefined torque limit. Individuals manually installing the pump 12, 14 on the pole 24 will have different strength capabilities for applying torque to the hand knob 48. The clutch mechanism 50 insures that a consistent clamping force is applied to the pole 24 and prevents overtightening, which insures that the torque required to release the clamp mechanism from the pole is consistent and well within the capabilities of most individuals.

The ratchet portion 40 of the clamp shaft 34 has ratchet teeth. Preferably the ratchet teeth comprise external threads 51. The threads 51 can be any type of helical threads without detracting from the invention, but more preferably the threads 51 are pull-type buttress threads. As is well known in the mechanical arts, buttress threads have a pressure, thrust or load flank that is nearly perpendicular (with less than ten, and more preferably about five to seven, and typically about five degrees inclination allowed for cutter clearance) to the thread axis of the shaft and a clearance flank, lead flank or thread angle that is about fifty to forty-five degrees. Preferably, the buttress threads utilized in this invention have a pressure flank 52 directed toward the proximal end 38 of the clamp shaft 34 and a lead flank 54 directed toward the distal end 36 of the clamp shaft 34.

A selectively releasable positioning means or travel control means 56 is movably mounted on the clamp body 26. The travel control means 56 includes a release button 58 that has at least one pawl 59 adapted to matingly engage the threads 51 on the clamp shaft 34 and means for biasing the pawl 59 into engagement with the threads 51. The release lever or button 58 and pawl 59 are shown as a unitary body; however, it will be understood that the release lever 58 and pawl 59 may be provided as separate pieces. The release button 58 is movably mounted in a hole 60 in the first jaw 30. The hole 60 intersects the clearance hole 42 as shown. The release button 58 is preferably an elongated pin with a slot 62 extending transversely therethrough. The slot 62 receives the clamp shaft 34 and has a length greater than the major diameter of the threads 51 on the clamp shaft 34. The width of the slot 62 is slightly greater than the major diameter of the threads 51. The slot 62 includes the pawl 59 as a portion thereof and has a thread on a wall thereof for matingly engaging the ratchet portion 40 of the clamp shaft 34. The pawl 59 is normally biased into mating engagement with the ratchet portion 40 of the clamp shaft 34 by a biasing means 64 (such as a spring or other similar device) operatively interposed between the release button 58 and the first jaw 30.

In operation, the travel control means 56 is configured and arranged to normally resist axial movement of the clamp shaft 34 in a direction away from the pole-receiving slot 28. The travel control means 56 also permits a user to apply an axial force to the clamp shaft 34 sufficient to overcome the biasing force of the biasing means 64, to permit slide-ratcheting axial movement of the clamp shaft 34 in a direction toward the opening or pole-receiving slot 28.

Alternatively, in some applications it is desirable to prevent slide-ratcheting axial movement of the clamp shaft 34 if axial force is inadvertently applied to the clamp shaft 34. In this case the biasing means 64 is selected to provide sufficient spring force to prevent normal user force on the clamp shaft 34 from causing slide-ratcheting axial movement of the clamp shaft 34 without the user also deactivating the travel control means 56.

A biasing means 66 (such as a spring or other similar device) is operatively interposed between the first jaw 30 and a ledge 68 on the clamp shaft 34. A bellows element 70 encloses the clamp shaft 34 and biasing means 66. The bellows element 70 protects a user from contacting the clamp shaft 34 and biasing means 66 moving parts.

Figure 4:
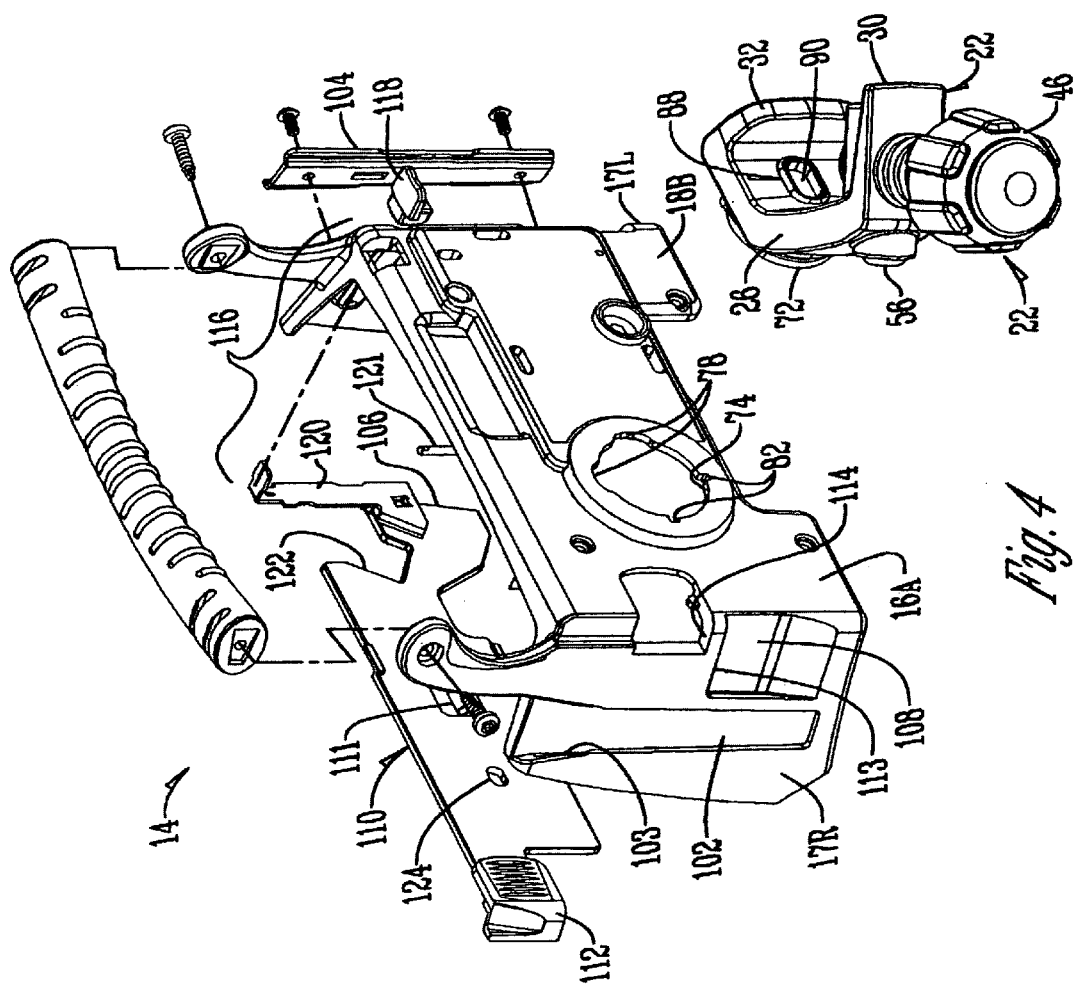
FIG. 4 is a partial rear exploded perspective view of the device of FIG. 2A.

As best seen in FIGS. 3 and 4, the clamp mechanism 22 is adapted to be rotatably associated with the medical device housing 16A or 16 (not shown). The clamp mechanism 22 includes a clamp lug 72 which rotationally mates with a housing lug 74. The clamp lug 72 includes extended ear elements 76 that correspond in shape and size to ear recesses 78 in the housing lug 74. The ear recesses 78 receive the extended ear elements 76. Once the clamp mechanism 22 is rotated, the clamp lug 72 mates with housing lug 74 to removably secure the clamp mechanism 22 to the medical device housing 16A.

A pivot latch 80 is movably mounted on the clamp body 26. The pivot latch 80 permits an operator to selectively lock the clamp mechanism 22 in a select one of a plurality of rotational positions with respect to the housing 16A. These rotational positions are defined by the recesses 82 of the housing lug 74. The pivot latch 80 is normally biased into mating engagement with the recesses 82 of the housing lug 74 by a biasing means 84 (such as a spring or other similar device) operatively interposed between the pivot latch 80 and the clamp body 26.

Figure 5:
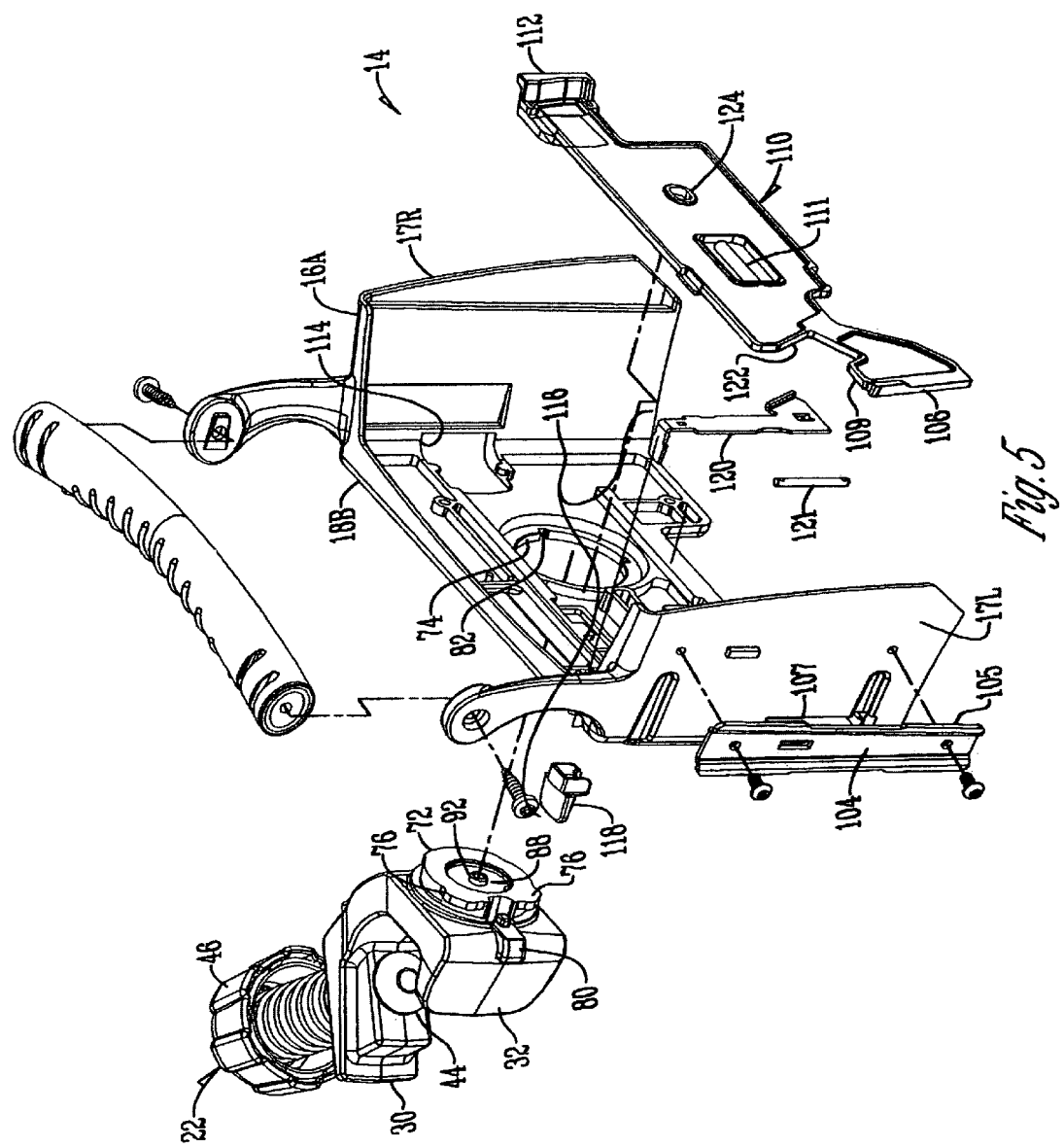
FIG. 5 is a partial front exploded perspective view of the device of FIG. 2A.
Figure 5A:
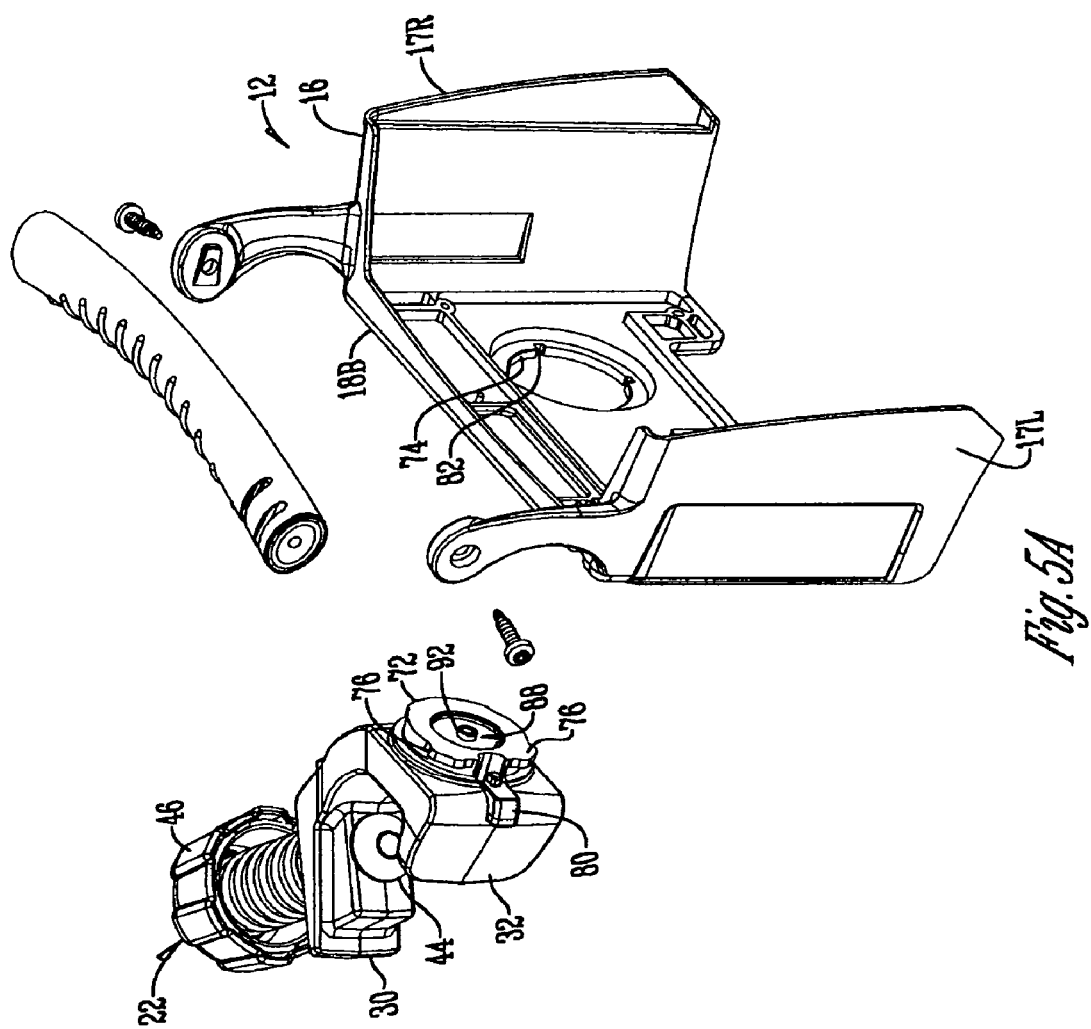
FIG. 5A is a partial front exploded perspective view of the device of FIG. 1, which is also the device on the right when viewed as in FIG. 2.

As best seen in FIGS. 3-5, the clamp body 26 has a hole 86 therein for slidably receiving a locking element 88. As will be discussed in greater detail below, the locking element 88 applies force on a component of the medical device 14 when the clamp body 26 is affixed to a support member 24 (FIG. 2A). As shown, the locking element 88 includes a support contact element 90 that contacts a support member 24 and is connected to a transfer pin 92 for locking the selected component of the medical device 14 to a restricted range of motion, and a main body 93 extending between the support contact element 90 and the transfer pin 92. Although the main body 93, support contact element 90, and transfer pin 92 are shown as a unitary member, one skilled in the art will appreciate that they can be separate components without detracting from the invention. For example, the contact element 90 and transfer pin 92 can be a unitary member that is movable with respect to the main body 93 or all three parts can be separate components.

The transfer pin 92 is normally biased toward the pole-receiving slot 28 and away from the housing 16A by a biasing means 94 (such as a spring or other similar device) operatively interposed between the main body 93 and the clamp body 26. A washer 95 provides a seat for the biasing means 94 and retains the main body 93 in the opening 86 when a retaining ring 97 is installed in a retaining groove 99 in the opening 86. The washer 95 has a hole 101 through which the transfer pin 92 slidably extends. Thus when the clamp body 26 is mounted on the housing 16A the biasing means 94 is also operatively interposed between the housing 16A and the main body 93.

Other designs of locking element are contemplated. For instance, the locking element 88 could apply only a frictional force to the selected component of the medical device 14.

As best seen in FIGS. 2A, 4 and 5, the medical device 14 includes a first matable element 102 positioned on the side wall 17R and a second matable element 104 positioned on the side wall 17L. The first matable element 102 is formed as a female T-slot in the housing 16A. The second matable element 104 is formed as a male T-slide attached to the housing 16A. Alternatively, the first matable element 102 is formed as a female dovetail in the housing 16A, and the second matable element 104 is formed a male dovetail attached to the housing 16A. Another alternative embodiment is to merely provide at least one of the opposite sides of the medical devices 14R, 14L with a matable element for detachably interconnecting to the matable element of the other medical device and attaching the first and second medical devices together. In other words, the unused matable elements in FIGS. 2A, 4, 5 and 5A could be removed or omitted.

The first matable element 102 includes a ramped portion 103 at its upper end. The ramped portion 103 allows for a greater degree of freedom when a user initially mates the first matable element 102 to the second matable element 104. Likewise, the second matable element 104 includes a tapered portion 105 at its lower end. The tapered portion 105 allows for a greater degree of freedom when a user initially mates the first matable element 102 to the second matable element 104. Without such ramped portion 103 and/or tapered portion 105, the first matable element 102 and second matable element 104 would need to be precisely aligned to properly mate together.

Although it may differ in the clinical function or task it performs, with respect to its attachment or connectology features, the second medical device 14R is substantially identical to the first medical device 14L. The second medical device 14R includes second matable element 104 positioned on the side wall 17L for detachably interconnecting to the corresponding first matable element 102 of the first medical device 14L, attaching the first and second medical devices 14L, 14R.

Once first and second medical devices 14L, 14R are joined, a latch element 106 extending through latch port 107 in the second medical device 14R side wall 17L mates with a corresponding latch notch 108 on the first medical device 14L side wall 17R. The latch element 106 detachably locks the first and second devices 14L, 14R together, and prevents the first and second matable elements 102 and 104 from being uncoupled.

The latch element 106 is formed as a portion of a transfer plate 110. The transfer plate 110 extends through both side walls 17L and 17R of the device 14. The transfer plate 110 also includes a biasing means 111 (such as a spring or other similar device) operatively interposed between the transfer plate 110 and the housing 16A for laterally biasing the latch element 106 toward the latch notch 108. When the latch element 106 is engaged to a corresponding latch notch 108, the transfer plate 110 is slightly displaced relative to the housing 16A and the side walls 17L and 17R. This displacement causes a blocking element 112 of the transfer plate 110 to extend through a blocking port 114 in the second medical device 14R side wall 17L. When the blocking element 112 is extended, no additional medical device can be joined to the second medical device 14R.

Figure 1A:
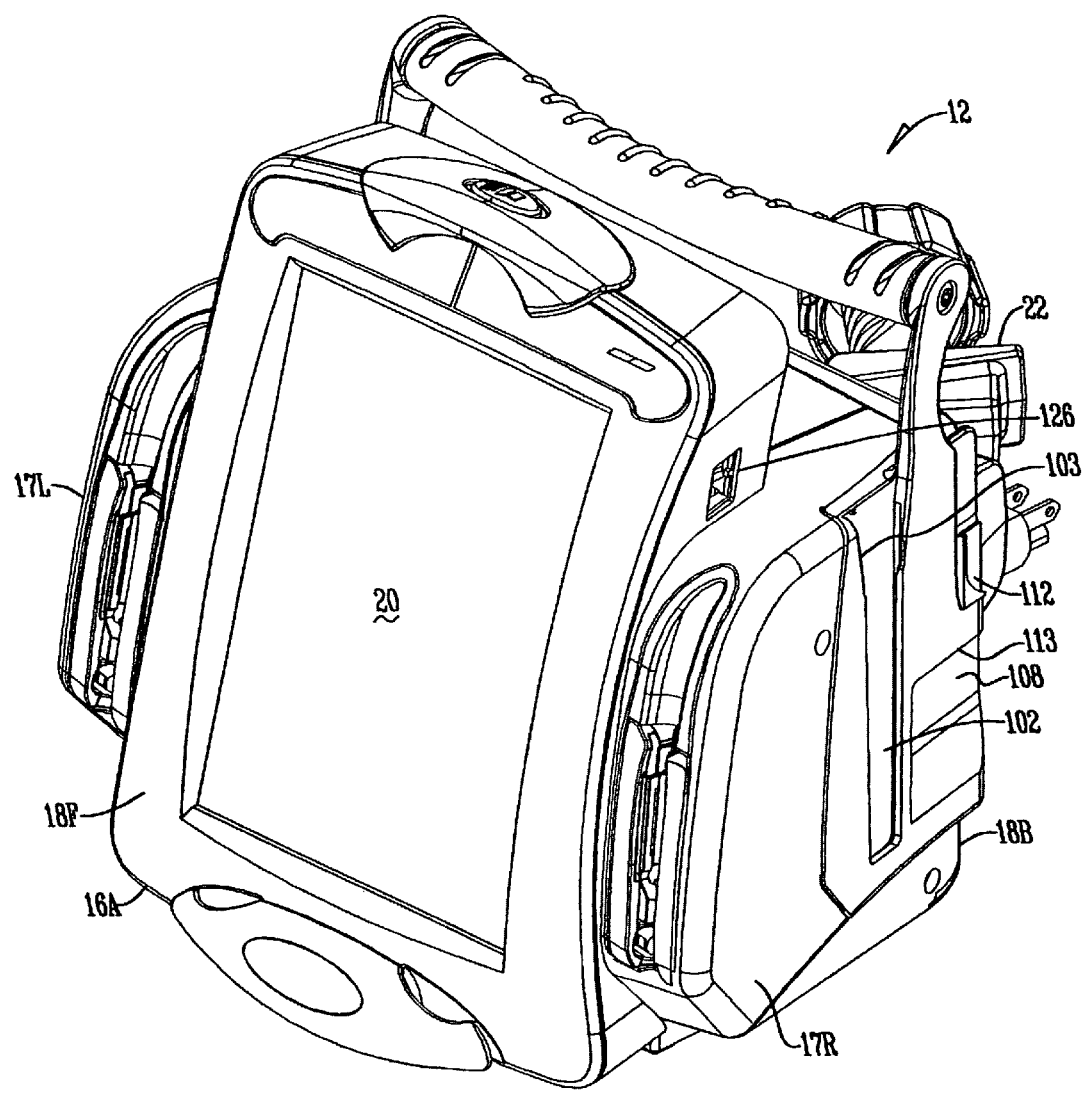
FIG. 1A is a front perspective view of another medical device adapted for use in a medical device system according to the present invention.

As best seen in FIGS. 1, 4 and 5, a latch post 109 is formed as a portion of a transfer plate 110. The latch post 109 is located along an upper edge of latch element 106 and mates with a corresponding undercut portion (not shown) located on the upper surface 113 of latch notch 108. In normal operation, the latch post 109 does not engage undercut portion of latch notch 108. However, in situations where a user is carrying two devices 12, 14 or 14L, 14R connected together by the handle of the right most device (14R), the latch post 109 prevents unintentional release of the latch element 106. Without latch post 109 and the undercut on surface 113, such an unintentional release would cause the left most device (14L or 12) to release out of attachment and to free fall. However, with the latch post 109, the latch element 106 mates with the corresponding undercut portion of latch notch 108 when the two devices (12 and 14R or 14L and 14R) are lifted only by the handle of the right most device (14R), and thus only slight relative movement is permitted between the two devices.

As best seen in FIGS. 2A, 4 and 5, likewise, the blocking element 112 of the first medical device 14L abuts the second medical device 14R side wall 17L, and prevents the transfer plate 110 of the first medical device 14L from moving. Thus, the latch element 106 of the first medical device 14L is likewise prevented from moving, which will also block any additional medical device from being joined to the side wall 17L of first medical device 14L.

Thus both blocking element 112 of the second medical device 14R and the latch element 106 of the first medical device 14L act as a blocking means for preventing a third medical device 12 or 14 from attaching to either the first or second medical device 14L or 14R once the first and second medical devices 14L, 14R are attached. This operation of a blocking means for preventing the connection of a third medical device 12 or 14 prevents the support surface 24 from bearing too much weight or from having an unbalanced weight placed on it sufficient to topple the support surface 24. For instance, the support surface 24 will typically be an IV stand. As shown in FIG. 2, two devices 14L, 14R (as explained below, device 12 could replace the device 14L) joined together place a somewhat unbalanced weight placed on the support surface 24. The two of the devices 12 and/or 14 joined together do not have a weight sufficient to topple the support surface 24. However, if a third medical device 12 or 14 was attached, there could be an unbalanced weight sufficient to topple the support surface 24. Thus, the blocking means prevents the user from the hazard of hanging too many connected medical device 12 or 14 from the support surface 24.

When it is desired to uncouple the first and second medical devices 14L, 14R, a release element 116 on the second medical device 14R is actuated by the user. The release element 116 includes a tab 118 that permits the user to manually actuate the release element and base 120 extending from the tab 118 to contact the transfer plate 110 at a surface 122 thereof. The release element 116 also includes a biasing means 121 (such as a spring or other similar device) operatively interposed between the base 120 and the housing 16A for downwardly biasing the release element 116. When the release element 116 is actuated, the base 120 shifts the transfer plate 110, uncoupling the latch element 106 of the second medical device 14R from the corresponding latch notch 108 of the first medical device 14L. When this is done the user can uncouple the male matable element 104 of the second medical device 14R from the corresponding female matable element 102 of the first medical device 14L.

As best seen in FIGS. 2A, 4 and 5, once a lone first medical device 14L is attached to a support structure 24, the support structure 24 presses on the support contact element 90 of the locking element 88. The pressure on the support contact element 90 displaces the entire locking element 88, thus moving the transfer pin 92 towards transfer plate 110. The transfer pin 92 engages a corresponding pin slot 124 portion of the transfer plate 110, securing the transfer plate 110 to a restricted range of motion. The pin slot 124 is shown as a hole in the transfer plate 110, but may also be formed as depression in the transfer plate 110. However, where other designs of locking element are utilized, the pin slot 124 may not be an essential component. For instance, it is contemplated that the locking element 88 could apply only a frictional force to the transfer plate 110 of the medical device 14. In this case, the pin slot 124 would not be needed.

The pin slot 124 is oriented and arranged to receive the transfer pin 92, even in cases where two devices are joined (FIGS. 2 and 2A) and the device 14L is attached to the support structure 24. In this situation, the transfer plate 110 of device 14R is slightly displaced when the latch element 106 of device 14R is engaged to a corresponding latch notch 108 in either device 12 or 14L.

Once the locking element 88 secures the transfer plate 110 to a restricted range of motion, the latch element 106 remains in an extended position through latch port 107 in the medical device 14L side wall 17L. The restricted extended latch element 106 of the first medical device 14L will block any additional medical device from being joined to the side wall 17L of first medical device 14L. Thus the locking element 88 fixing the latch element 106 operates as a selective means for restricting the attachment of the second medical device 14R to only the side wall 17R of first medical device 14L when first medical device 14L has been previously secured to support structure 24. Accordingly, it can be seen that when a separate first medical device 14L has been secured to support structure 24, any attachment of another device (e.g. second medical device 14R) can only be made to a predetermined side, i.e., side wall 17R, of first medical device 14L.

This operation of a selective means for restricting the attachment of the second medical device 14R to only one side of the first medical device 14L lessens the potential for operator confusion when the second medical device 14R is being attached to a first medical device 14L that has been previously secured to support structure 24. For instance, where the first medical device 14L is a medical pump having defined first and second channels or pump mechanisms, when the first medical device 14L is attached by itself to support structure 24, there is little confusion as to where the first and second channels are located. Typically, the first channel will be located near side wall 17L and the second channel will be located near side wall 17R, with the user interface touch screen 20 disposed between the first and second channels. However, in instances where a second medical device 14R having defined third and fourth channels is later added to the first medical device 14L, placement of the second medical device 14R adjacent to the side wall 17L would increase the potential for user confusion. In such a case, the set of devices 14L, 14R would have a series of channels running from left to right in the following order: the third channel, the fourth channel, the first channel, and then the second channel. In order to prevent such confusion of channels in the use of the medical device system 10, 10A of the present invention, the selective means restricts the attachment of the second medical device 14R to only the side wall 17R of first medical device 14L, so that the channels running from left to right will have the following order: the first channel, the second channel, the third channel, and then the fourth channel.

As best seen in FIGS. 1, 2 and 5, while the above system 10A for interconnecting medical devices is operable with any device 14 having the same interconnectable design, it is also designed to operate with a device 12 of system 10. As best understood in view of FIGS. 5 and 5A, the portable medical device 12 includes some features similar to the device 14, so that the devices 12 and 14 can be joined together; however, several components found in the device 14 (latch port 107, transfer plate 110, blocking port 114, and release element 116) are not included in the device 12. This design permits a user to distinguish between the two devices 12, 14, prevents undesirable arrangements and combinations, and also reduces the manufacturing cost as well as improving the reliability of the device 12 as compared to the device 14.

Specifically, the device 12 includes a single matable element 102 on side wall 17R. The single matable element 102 is formed as a female T-slot slot for mating with corresponding male T-slide 104 from the device 14. The device 12 also includes a latch notch 108 for mating with corresponding latch element 106 from the device 14.

However, unlike the device 14, the device 12 has no elements on its opposite side wall 17L for connecting to any other medical device 12 or 14. This lack of elements on one side wall 17L of device 12, allows the device 12 to prevent a second medical device 14 from being attached to the left of a first device 12, including when the first device 12 is secured to a support 24. Thus the lack of elements on one side wall 17L of device 12 acts as a selective means for restricting the attachment of a second medical device 14 to only one of the opposite sides of the first medical device 12.

The lack of elements on one side wall 17L of first device 12 also prevents any device 12 or 14 from attaching to that side wall 17L of the first device 12. The latch notch 108 of the first device 12 also acts to activate the blocking element 112 on the second device 14 to prevent a third medical device 12 or 14 from being joined to the second device 14. Thus the lack of elements acts as a blocking means for preventing a third medical device 12 or 14 from attaching to either the first or second medical devices once the first and second medical devices 12, 14 are attached to one another.

As best seen in FIGS. 1, 1A, 2 and 2A, each of the medical devices 12, 14 includes at least one transceiver 126. The medical device 12 is provided with one transceiver 126 located on the side 17R of the device 12 that has the matable element 102 positioned thereon. Each medical device 14 is provided with one transceiver 126 on each side 17L and 17R of the device 14. The transceiver 126 (not shown) positioned on side 17R of the first medical device 14L is aligned with the corresponding transceiver 126 positioned on side 17L of the second medical device 14R for communication between the medical devices 14L, 14R once the medical devices 14L, 14R are attached. The aligned transceivers 126 permit the medical devices 14L, 14R to communicate to one another. The transceivers 126 can be adapted for wireless communication or can physically contact each other once aligned. The transceivers 126 can be of various types, including but not limited to infrared, blue tooth, or radio frequency. For instance, the aligned transceivers 126 permit the medical devices 14L, 14R to synchronize activities and/or share data including but not limited to: time, patient information, drugs in use, pressure, flow data, total infusion volume, and historical logged information.

As best seen in FIG. 6, an alternative clamping mechanism 222 of the present invention has a substantially rigid clamp body 226 that is pivotally and preferably removably attached to the pump housing 16 or 16A (not shown) and includes a pole-receiving slot 228 for receiving the pole (not shown). The clamp body 226 defines generally opposing first and second jaws 230, 232 that at least partially surround the pole-receiving slot 228.

A clamp shaft 234 is movably mounted on the first jaw 230. The clamp shaft 234 has opposite ends 236, 238 and a ratchet portion 240 therebetween. The first jaw 230 has a hole 242 formed therein, and more preferably therethrough, for receiving bushing 243 and the ratchet portion 240 of the clamp shaft 234. The distal end 236 of the clamp shaft 234 extends from the first jaw 230 toward the second jaw 232. A pressure pad 244 connects, or more preferably attaches, to the distal end 236. The proximal end 238 of the clamp shaft 234 has displacement means 246. Biasing means 266 (such as a spring or other similar device) is operatively interposed between the first jaw 230 and the clamp shaft 234. A bellows element 270 encloses the clamp shaft 234 and biasing means 266.

A selectively releasable positioning means or travel control means 256 is movably mounted on the first jaw 230. The travel control means 256 includes a release lever 258 that has at least one pawl 259 adapted to matingly engage the ratchet portion 240 on the clamp shaft 34 and means for biasing the pawl 259 into engagement with the ratchet portion 240. The release lever 258 and pawl 259 are shown as a unitary body; however, it will be understood that the release lever 258 and pawl 259 may be provided as separate pieces. The release lever 258 is positioned adjacent a hole 260 in the first jaw 230. The release lever 258 is pivotally mounted to the first jaw 230 by pin 261. The pawl 259 is positioned exterior to the first jaw 230 at an outer end of the hole 242, within the pole-receiving slot 228. The pawl 259 is normally biased into mating engagement with the ratchet portion 240 of the clamp shaft 234 by a biasing means 264 (such as a spring or other similar device) positioned within hole 260, and which is operatively interposed between the release lever 258 and the first jaw 230.

In operation, the travel control means 256 is configured and arranged to normally resist axial movement of the clamp shaft 234 in a direction away from the pole-receiving slot 228. The travel control means 256 also permits a user to apply an axial force to the clamp shaft 234 sufficient to overcome the biasing force of the biasing means 264, to permit slide-ratcheting axial movement of the clamp shaft 234 in a direction toward the opening pole-receiving slot 228.

Alternatively, in some applications it is desirable to prevent the slide-ratcheting axial movement of the clamp shaft 234 if axial force is inadvertently applied to the clamp shaft 234. In this case the biasing means 264 is selected so as to have sufficient spring force to prevent normal user force on the clamp shaft 234 from causing slide-ratcheting axial movement of the clamp shaft 234 without the user also deactivating the travel control means 256.

It is therefore seen that this invention provides an improved system of interlockable portable medical devices that only allows two medical devices to be joined together. The invention also provides an improved system of interlockable portable medical devices. In addition, the invention provides an improved clamp mechanism, for mounting a medical device to a support member, which restricts the attachment of a second medical device to only one side of a first medical device when the clamp mechanism is attached to a support member. Finally, the invention provides an improved clamp mechanism that permits quick slide-ratcheting axial movement of the clamp shaft.

It is therefore seen that this invention will accomplish at least all of its stated objectives.

What is claimed is:

1. A clamp mechanism for mounting a medical device to a support member, comprising:
   a clamp body defining a first jaw, a second jaw and an opening therebetween adapted to receive a support member;
   a clamp shaft including a forward end for extending into the opening, a rearward end, and an intermediate portion having a longitudinal axis and being mounted for axial movement on the first jaw of the clamp body;
   ratchet and pawl means operatively interposed between the intermediate portion of the clamp shaft and the clamp body,
   the ratchet and pawl means comprising ratchet teeth and a pawl;
   biasing means for yieldingly urging the pawl and ratchet teeth into engagement with a biasing force; and
   the biasing means, the ratchet teeth, and the pawl being configured and arranged to normally resist axial movement of the clamp shaft in a direction away from the opening and, upon application of an axial force to the clamp shaft sufficient to overcome the biasing force of the biasing means, to permit slide-ratcheting axial movement of the clamp shaft in a direction toward the opening.

2. A clamp mechanism in accordance with claim 1, wherein the clamp body has a hole therein for slidably receiving a locking element the locking element adapted to apply force on a component of the medical device when the clamp body is affixed to a support member.

3. A clamp mechanism in accordance with claim 1, wherein the first jaw and the second jaw are stationary.

4. A clamp mechanism in accordance with claim 1, wherein the first jaw of the clamp body has a clamp shaft receiving bore therein for slidably receiving the clamp shaft.

5. A clamp mechanism in accordance with claim 1, wherein the ratchet teeth are external threads formed on the intermediate portion of the clamp shaft, and wherein the threads have a forward lead flank and a rear load flank, the leading flank extending rearward to form an acute angle with a longitudinal axis of the clamp shaft and the load flank extending perpendicular to the longitudinal axis of the clamp shaft.

6. A clamp mechanism in accordance with claim 1, further comprising a release mechanism for overcoming the biasing force of the biasing means and disengaging the pawl and ratchet teeth, thereby permitting axial movement of the clamp shaft in the direction away from the opening.

7. A clamp mechanism in accordance with claim 6, wherein the release mechanism and the pawl means are a unitary body.

8. A clamp mechanism in accordance with claim 6, wherein the first jaw has a release bore therein and the release mechanism is an elongated pin slidably mounted in the release bore.

9. A clamp mechanism in accordance with claim 6, wherein the release mechanism has an adjustment slot extending therethrough for receiving the clamp shaft, the ratchet portion of the clamp shaft having threads with a major diameter and the adjustment slot having a length greater than the major diameter of the threads on the clamp shaft, the pawl being a portion of a wall of the adjustment slot having a thread thereon for matingly engaging the ratchet portion of the clamp shaft.

10. A clamp mechanism in accordance with claim 1, further comprising a hand knob attached to the second end of the clamp shaft.

11. A clamp mechanism in accordance with claim 10, further comprising a clutch mechanism operatively interposed between the hand knob and the clamp shaft, the clutch mechanism being adapted to prevent overtightening of the clamp shaft against a pole beyond a given torque value.

12. A clamp mechanism in accordance with claim 1, wherein the clamp mechanism is adapted to be rotatably associated with the medical device.

13. A clamp mechanism in accordance with claim 12, wherein the clamp mechanism includes a pivot latch adapted to selectively lock the clamp mechanism in a select one of a plurality of rotational positions with respect to the medical device.

14. A clamp mechanism for mounting a medical device to a support member, comprising:
   a clamp body defining a first jaw, a second jaw and an opening therebetween adapted to receive a support member;
   a clamp shaft including a forward end for extending into the opening, a rearward end, and an intermediate portion having a longitudinal axis and being mounted for axial movement on the first jaw of the clamp body;
   ratchet and pawl means operatively interposed between the intermediate portion of the clamp shaft and the clamp body, the ratchet and pawl means comprising ratchet teeth and a pawl;
   biasing means for yieldingly urging the pawl and ratchet teeth into engagement with a biasing force;
   the biasing means, the ratchet teeth, and the pawl being configured and arranged to normally resist axial movement of the clamp shaft in a direction away from the opening; and
   a release mechanism for overcoming the biasing force of the biasing means and disengaging the pawl and ratchet teeth, thereby permitting axial movement of the clamp shaft in the direction away from the opening; wherein the release mechanism and the pawl means are a unitary 10 body.

15. A clamp mechanism in accordance with claim 14, wherein the ratchet teeth are external threads formed on the intermediate portion of the clamp shaft.

16. A clamp mechanism in accordance with claim 15, wherein the threads have a forward lead flank and a rear load flank, the leading flank extending rearward to form an acute angle with a longitudinal axis of the clamp shaft and the load flank extending perpendicular to the longitudinal axis of the clamp shaft.

17. A clamp mechanism in accordance with claim 14, wherein the first jaw of the clamp body has a clamp shaft receiving bore therein for slidably receiving the clamp shaft.

18. A clamp mechanism in accordance with claim 14, wherein the first jaw has a release bore therein and the release mechanism is an elongated pin slidably mounted in the release bore.

19. A clamp mechanism in accordance with claim 14, wherein the release mechanism has an adjustment slot extending therethrough for receiving the clamp shaft, the ratchet portion of the clamp shaft having threads with a major diameter and the adjustment slot having a length greater than the major diameter of the threads on the clamp shaft, the pawl being a portion of a wall of the adjustment slot having a thread thereon for matingly engaging the ratchet portion of the clamp shaft.

20. A clamp mechanism in accordance with claim 14, wherein the release mechanism includes a release lever pivotally mounted to the first jaw.

21. A clamp mechanism in accordance with claim 20, wherein the release mechanism including the release lever and pawl means are located on the exterior of the first jaw.

22. A clamp mechanism in accordance with claim 14, further comprising a hand knob attached to the second end of the clamp shaft.

23. A clamp mechanism in accordance with claim 22, further comprising a clutch mechanism operatively interposed between the hand knob and the clamp shaft, the clutch mechanism being adapted to prevent overtightening of the clamp shaft against a pole beyond a given torque value.

24. A clamp mechanism in accordance with claim 14, wherein the clamp mechanism is adapted to be rotatably associated with the medical device.

25. A clamp mechanism in accordance with claim 24, wherein the clamp mechanism includes a pivot latch adapted to selectively lock the clamp mechanism in a select one of a plurality of rotational positions with respect to the medical device.

* * * * *